United States Patent
Gobbi et al.

(10) Patent No.: US 6,715,878 B1
(45) Date of Patent: Apr. 6, 2004

(54) APPARATUS FOR MEASURING VISUAL PERFORMANCE

(75) Inventors: Pier Giorgio Gobbi, Pavia (IT); Stefano Bozza, Milan (IT); Francesco Carones, Milan (IT); Rosario Brancato, Milan (IT)

(73) Assignee: Fondazione Centro S. Raffaele del Monte Tabor, Milan (IT)

( * ) Notice: Subject to any disclaimer, the term of this patent is extended or adjusted under 35 U.S.C. 154(b) by 43 days.

(21) Appl. No.: 10/088,091

(22) PCT Filed: Sep. 25, 2000

(86) PCT No.: PCT/EP00/09465
§ 371 (c)(1), (2), (4) Date: Jun. 25, 2002

(87) PCT Pub. No.: WO01/21062
PCT Pub. Date: Mar. 29, 2001

(30) Foreign Application Priority Data

Sep. 24, 1999 (IT) .......... MI99A1991

(51) Int. Cl.$^7$ .......... A61B 3/02
(52) U.S. Cl. .......... 351/243
(58) Field of Search .......... 351/205, 206, 351/208, 221, 237, 239, 243, 245, 246, 244, 222

(56) References Cited

U.S. PATENT DOCUMENTS 5,592,247 A * 1/1997 Trokel .......... 351/239
5,969,792 A * 10/1999 Ginsburg .......... 351/243
6,244,713 B1 * 6/2001 Hayashi .......... 351/243

* cited by examiner

Primary Examiner—George Manuel
(74) Attorney, Agent, or Firm—Oblon, Spivak, McClelland, Maier & Neustadt, P.C.

(57) ABSTRACT

An apparatus for measuring visual performance suitable for carrying out various visual functionality tests in controlled and variable opening conditions of the pupils of a subject. The apparatus uses optic systems for the control of ambient brightness, and uses systems of illumination, observation, and measurement of the pupillary dimensions.

23 Claims, 2 Drawing Sheets

APPARATUS FOR MEASURING VISUAL PERFORMANCE

The present invention refers to an apparatus for measuring visual performance for ophthalmologic examinations. Observation of the visual acuity of both eyes, of a subject being examined, is the basic procedure of every ophthalmologic examination aimed at quantitatively assessing visual performance and the extent of any refractive correction necessary to optimise the functionality of the vision apparatus.

Such observation is normally performed by covering one eye at a time, of the subject being examined, and sequentially subjecting the individual to a series of characters and/or graphic signs of progressively smaller size; the patient is asked to recognise the characteristics of each character and/or figure shown, until the discrimination limit is reached. Since each character size corresponds to a progressive value, increasing with a decrease in size, normally expressed as a fraction (e.g. $4/10$ or $20/50$ or $6/15$) or as a decimal (e.g. 0.4), the value corresponding to the smallest character sizes correctly recognised corresponds to the visual acuity of the eye being examined.

Measurement of visual acuity is usually performed in mesopic illumination conditions (semi-darkness) and the characters to be recognised are shown at a typical distance of 4–6 meters from the subject; this can be with the naked eye, if emmetropic (i.e. uncorrected visual acuity) or with corrective ocular prostheses worn (spectacles or contact lenses) and, hence, concerns visual acuity with correction.

The characters to be recognised may be displayed on externally illuminated signs or on translucent backlit panels (optotypes in both cases) or visualised on an opaque screen through a light projector; the characters are generally black on a transparent background and normally include stylized capital letters of the alphabet, and arranged on a single square grid. Actually, various print style and selection standards of the same letters exist, to produce a set of characters of equal legibility (e.g. Snellen or Sloan).

Numbers can also be used in addition to letters, while other standards use a single character (e.g. Albini's E or Landolt's broken C test), the orientation of which is varied (top, bottom, right, left): these tests are meant for illiterate individuals, namely pre-school children.

The character size may, in turn, follow a linear or geometrical progression, with different ratio values between successive terms; the most widespread scale is logMAR, in which the ratio is $10\sqrt{10} \approx 1.259$.

A further visual functionality examination of considerable importance is the contrast sensitivity test. Once again this is performed by covering one eye at a time and presenting the patient with a sequence of figures characterised by black and white linear monochromatic reticula.

The reticula are of two types: square and sinusoidal wave, i.e. their brightness outline varies perpendicularly, like a square or sinusoidal wave, to the direction of the reticulum lines.

Within the sequence, the reticula vary both in terms of spatial frequency (number of cycles per view angle unit subtended by the observation point of the patient, as well as contrast (defined as the ratio between the difference: maximum brightness-minimum brightness and their combined total); the visibility of the reticula decreases with an increase in the spatial frequency and a decrease in contrast.

Of current use in clinical tests are reticula with a frequency of 1–30 cycles per grade and contrasts between 100% and 10%; they are usually made of shapes printed on card or glass (backlit in this case), to be observed in photopic conditions from a typical distance of 2 meters.

The subject being examined is invited to recognise the orientation of each reticulum of the sequence and, for each spatial frequency, the lowest contrast value correctly recognised represents the visibility threshold; colour reticula can also be used (especially of blue-yellow type) to distinguish retinal pathologies.

Other significant visual functionality tests include colour sense examinations (Holmgren's test, Ishihara's test) and light sense examinations (visual acuity recovery test following macular halation).

All the tests described are produced in stationary conditions and supply the results relating to the visual performance of a subject at a certain moment. However, it is known that visual performance is greatly influenced by ambient brightness and pupillary diameter, mainly as a consequence of the increase in optic aberrations with the same diameter.

Therefore, conventional apparatuses are incapable of quantifying an identical visual performance, chosen from a range of possibilities at different pupillary opening values basically corresponding to photopic type ambient brightness (full light), mesopic (semi-darkness) and scotopic (dark) conditions.

Therefore the aim of the present invention is to demonstrate a measuring apparatus of visual performance for ophthalmologic examinations, which obviates the above mentioned drawbacks, allowing the various visual functionality tests to be carried out in controlled and variable pupillary opening conditions of a subject, by controlling the ambient brightness and measurement of the pupillary diameter.

Another aim of the present invention is to demonstrate a measuring apparatus of visual performance of a patient which allows the assessment of such performance without the same being, in any way, influenced by the ambient illumination conditions, in which measurement is made, and hence, by the pupillary diameter of the eye being examined.

Another aim of the present invention is to produce an apparatus for measuring visual performance, which allows such performance to be assessed without the it being, in any way, influenced by optic aberrations.

A further aim of the present invention is to produce an apparatus for measuring visual performance which avoids any alteration of the outcome of the visual acuity test.

Not least, the aim of the present invention is to produce an autonomous apparatus for measuring visual performance which reduces the need for operator presence and, at the same time, maintaining essential levels of reliability and flexibility, compared to conventional apparatuses.

Such aims are reached by an apparatus for measuring visual performance according to claim 1, to which reference is made for the sake of brevity.

Advantageously, the apparatus, subject of the present invention, is able to produce the various visual functionality tests of a complete ophthalmologic examination in controlled and variable pupillary opening conditions of the subject being examined, by controlling ambient brightness and measurement of the pupillary size of the above mentioned subject.

It is, in fact, known that visual performance is largely influenced by pupillary diameter, mainly as a consequence of the increase in optic aberrations with the same diameter.

By way of a suitable measurement process, the apparatus is thus able to quantify an identical visual performance, chosen from a range of possibilities, at different pupillary opening values e.g. at 3, 5, 7 mm; values basically corresponding to the photopic, mesopic and scotopic conditions.

The adoption of random character sequences produced by a computer eliminates any chance of the patient memorising them and thus altering the test results.

The implementation of the headset form of apparatus for the patient being examined, accompanied by voice recognition and synthesis circuits, creates a largely autonomous measurement station, which reduces the need for operator intervention.

In addition, the various test results are memorizable and available for printing and statistical processing.

Use of the apparatus is, in short, particularly important in establishing the basic visual performance level in patients undergoing refractive surgery and for comparing its post-surgery development.

Besides, the test is useful for individuals working in extreme light environments, for instance vehicle drivers or airline pilots.

Further aims and advantages of the present invention will become apparent from the description that follows and from the enclosed designs, supplied simply as explanatory, non-limiting examples, in which.

Figure 1:
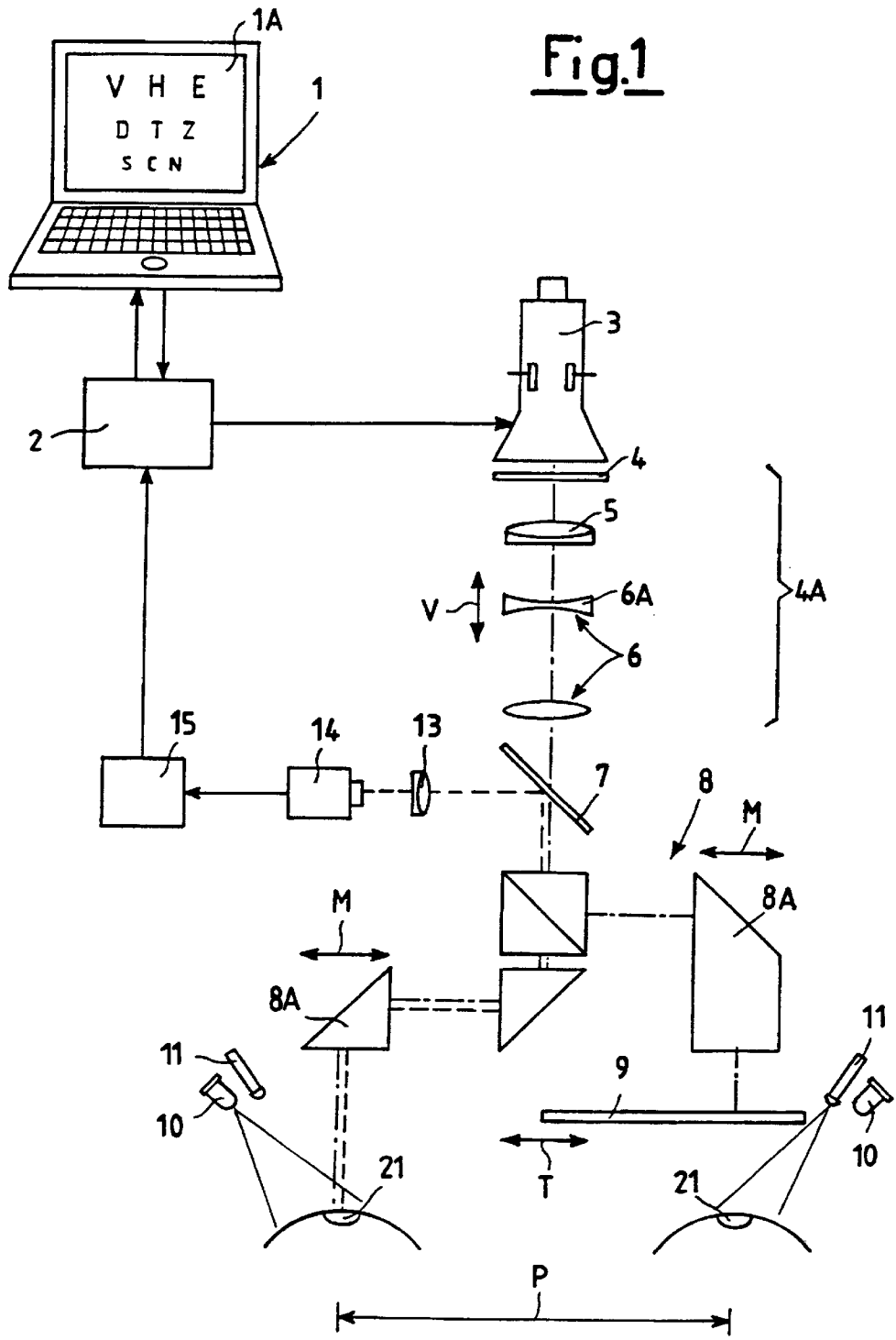
FIG. 1 represents a schematic view of a first embodiment relating to an apparatus for measuring visual performance, according to the present invention.

With reference to the figures mentioned, 1 denotes an electronic central processing unit, complete with a screen 1A and suitable for the production, using a special pilot application program, of characters and/or graphic signs on screen 1A, which are useful for determining the visual functionality of a patient being examined.

3 denotes a visualization device of the characters, figures and/or signs, appropriately controlled by a computer graphics board or scan converter 2, which is connected to the central processing unit 1. In particular, in preferred and non-limiting embodiments, the colour or monochromatic visualization device 3, may consist of a cathode-ray tube (CRT) or liquid crystal display (LCD) or a plasma or electroluminescent viewer.

Moreover, 4A denotes, as a whole and generically, an optic conjugation system including a series of lenses and mirrors, so arranged as to form a real or virtual image of the visualization device 3 screen, which is usually formed on a plane, set to infinity, with an exactly definable angular magnification; the optic conjugation system 4A may include, in preferred but nonlimiting embodiment examples, optic means 5, known in themselves, able to compensate for the refractive error (spherical and cylindrical) of an observer, within a suitable interval of values; in addition it may include means to compact the optic path, such as a focal systems or units 6, and optic filters 4, also these being known in themselves, of neutral or chromatic type, to vary the contrast or the image colour, respectively.

8 then indicates an optic system suitable to produce the division of the image made on two channels with equal brightness, in order to allow the binocular observation of the same image by the subject being examined. With regard to this, the optic system 8 includes parts 8A (prisms or equivalent), which may be moved according to the direction indicated by the arrows M, so as to be able to vary the separation between the observation eyepieces, adapting it to the interpupillary distance P of the subject being examined, without altering the image characteristics.

Figure 2:
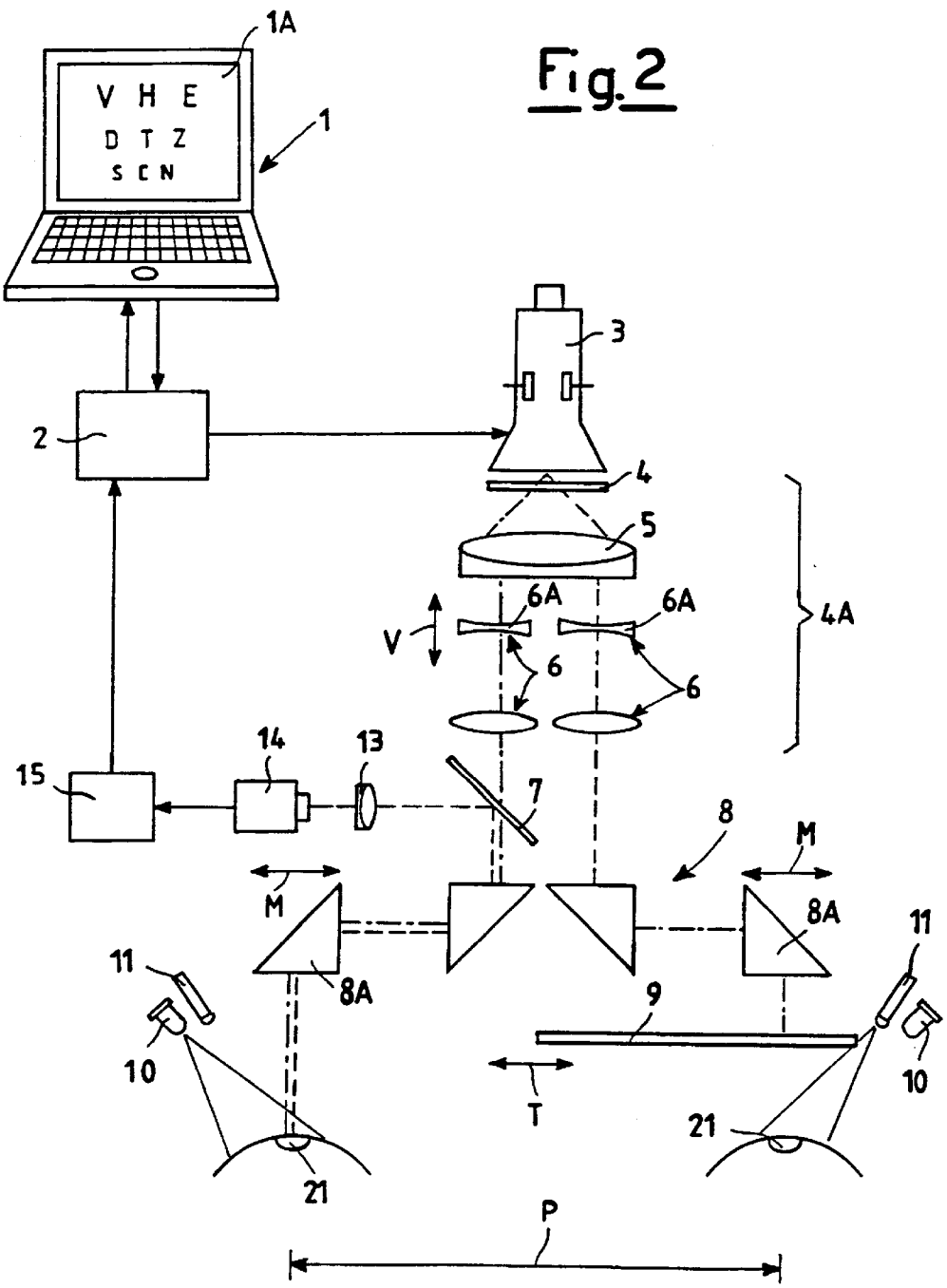
FIG. 2 represents a schematic view of a second embodiment relating to an apparatus for measuring visual performance, according to the present invention.

Finally 13, 14 indicate an observation and measuring device of each pupil 21 dimension of the subject being examined which, in preferred and non-limiting embodiments, may comprise of a televisual sensor (CCD or CID type) or a matrix detector, denoted by 14 in the figures and matched with a lens 13 to focus each pupil 21 of the patient; the signal of the image produced by the device 13, 14 and schematized as a dotted line in FIGS. 1 and 2 is analysed by an electronic circuit 15, which extracts, from the above mentioned signal, information relating to the pupil sizes 21 of the observer (such as, for example, the diameter or area), converting it into digital form and transmitting it to the central processing unit 1; the observation device 13, 14 measures the pupil sizes of the subject being examined in a sequential manner in time, e.g. with a frequency equal to or submultiple of the televisual scan frequency and can be formed by the same computer graphics board 2, capable of digitally memorising the pupil image data, together with the central processing unit 1, by a suitable image analysis application program. Alternatively, the observation device 13, 14 can be positioned at an angle with respect to the direction identified by the optic conjugation system 4A (the latter being outlined in the figures by dot-dash lines) or can be made collinear with respect to such direction, in which case, making use of a dichroic mirror 7 separating a spectral part of the electromagnetic radiation (that shown by a dotted line in the figures), coming from the eyeball of the patient; such an observation device 13, 14 may be present in one or both observation channels.

In addition, 10 generically denotes a device for the illumination of the pupils 21 of the subject being examined, by way of electromagnetic radiation which is not perceivable by the retina of the same (e.g. with infrared radiation), so as to provide a sufficient level of illumination for the entire observation and measurement system of the pupillary dimensions; the device 10 can be constituted, in preferred embodiment examples, by infrared LEDs with a wavelength of between 800–1400 nm and can include means suitable for polarizing the radiation emission. Finally, the above mentioned device 10 is controlled so as to switch on a first illuminator at the eye being measured, while a second illuminator is kept switched off.

9 denotes an optic path shutter relating to the pupils 21 of the patient which, moving in the direction of the arrows T, allows the optional obstruction of none, one or both eyes of the subject being examined, whereas 11 denotes an additional device for the illumination of the pupils 21 of the subject being examined with visible spectrum radiation, provided with an adjustable means of the light flux emitted, from zero (switched off) up to a maximum value which may be adjusted by the central processing unit 1; the illumination device 11 may include visible light incandescence bulbs, LEDs or fluorescent tubes and, in any case, the maximum light flux emitted must be able to induce a marked constriction (myosis) of the illuminated pupil 21 (up to a typical diameter equal to or less than 3 mm.). The illuminated pupil 21 corresponds to that of the eye which is not subjected to the measurement test of visual faculties (adelpho-eye), while the radiation direction is angled with respect to the visual axis, so as not to interfere with the central vision of the adelpho-eye and hence, the merging of the images, also of the eye subjected to measurement.

In preferred embodiment examples of the invention the entire apparatus, with the likely exception of the central processing unit 1 and computer graphics board 2, can be integrated in a headset, of the type used for indirect ophthalmoscope in ophthalmology or for virtual reality, which is worn by the patient. The headset is adjustable to all types of cranial variations and is firmly fixed to the head of the subject being examined, without causing problems or discomfort. In alternative embodiments, the apparatus may be securely fixed to a height adjustable motorised rest platform with a chin rest. The subject being examined sits in front of the motorised table placing his/her chin on the chin rest and forehead against the headrest, in the same way as an ophthalmologic biomicroscope (light and slot).

In preferred embodiment examples of the invention, the apparatus is divided into two parts: the visualization device 3 is placed, for instance, 4–6 meters from the patient and takes on sufficiently large dimensions to render superfluous the installation of the optic conjugation system 4A and the dichroic mirror 7 for optic separation of the image. The devices 9, 10, 11, 13, 14 of pupillary size observation, illumination and obstruction are integrated in a headset of the type described previously, while the headset and the visualization device 3 are connected to the electronic central processing unit 1 by means of suitable wires.

A typical measurement procedure of the visual functionalities is described as follows.

First of all, note that throughout the description, reference will be made, for purposes of simplicity, to the integral implementation of the apparatus, according to the invention, inside a headset to be fitted to the head of the patient being examined, even if, obviously, a virtually identical measurement procedure will also be carried out for the other cited embodiments.

In practice, the subject being examined wears the headset, which is then adjusted depending on the anatomical configuration of the head.

The operator assigned to carry out the measurement starts the measurement application program of visual performance of the subject on the central processing unit 1, for example by entering the personal data of the patient. At first a standard image of characters and/or figures is projected onto the visualization device 3 and the patient is asked to adjust the distance between the apparatus eyepieces until perfect merging of the two observed images is reached.

Thus the proper measurement stage of visual performance begins. The eyeball covering sequence is chosen (automatically or manually by the operator) on the basis of which shutter 9 obstructs the adelpho-eye and the illuminator 10 lights up at the eye being examined.

The image of the pupil 21 produced by the lens 13 and processed by circuit 15 and the computer graphics board 2 is reproduced on screen 1A of the central processing unit 1, in a box alongside the image produced by the same unit 1 and sent to the visualization device 3.

At the same time, circuit 15 supplies the pupillary diameter measured, which is reproduced on the screen 1A of unit 1.

The visible light illuminator 11 is initially switched off, so that the pupil 21 of the patient, being in excessive darkness, assumes wide dimensions (typically more than 6 mm; in scotopic conditions), whereas with an adequate adaptation to the dark, also rather excessive conditions of mydriasis can be reached (with a pupillary diameter of approx. 8–9 mm. after 10–30 minutes).

As a first step, a reference image is presented on the visualization device 3 and the patient can proceed to the fine focusing of such image; the ultimate aim is to compensate for any refraction defects of the eye or remains of refractive defects, even if already corrected with spectacles or contact lenses.

Such fine focusing adjustment can be performed, for example, moving in the direction of the arrow V, by adjusting a micrometric screw, the components denoted by 6A in FIGS. 1 and 2 of the a focal units 6.

In addition, for better results a dichromic test may be advisable: for this purpose, two columns of identical characters are shown on the visualizer 3, one column on a red background and the other on a green background.

The correct focusing of each subject occurs when the two character columns appear to have, for that given subject, the same legibility.

Lastly, in the event of a monochromatic visualizer 3 (black and white), it is necessary to insert a red-green dichromic filter at the front.

Under such conditions, a first test is carried out on one eye, based on a sequence of tests (chosen from the whole range of possible tests), which is pre-determined and memorised inside the central processing unit 1.

By way of example let us suppose that the first test relates to the visual acuity measurement on the logMAR scale, with white characters on a black background. In this case, the computer application program begins by presenting the patient with characters randomly selected from a collection of accepted characters, starting from a given angular size (e.g. 50'×50', corresponding to a visual acuity of $\frac{1}{10}$); the patient is asked to recognise the projected characters with the operator confirming the correctness of responses on the keyboard of the central processing unit 1.

Five characters are projected in sequence for each angular size and hence one moves onto the smaller size in the pre-chosen scale.

The procedure stops at the end of the sequence during which time either at least two recognition errors were made by the patient or the minimum possible size was reached, with the number of errors determining the measured value of visual acuity; the operator is able to see this value on the screen of the central processing unit 1, together with the mean value of the diameter of the pupil 21 examined, measured during the entire test duration, with both pieces of data memorised by the central processing unit 1.

Hence one passes onto a second visual performance examination of the subject, based on the programmed sequence; for instance visual acuity tests can be performed with black characters on a white background or with different characters (namely Landolt's C test or the Albini's E test) contrast sensitivity tests, colour tests and so on. In any case, for each test, the measurement of the mean pupil 21 diameter is memorised in unit 1, together with the final result of the corresponding test.

Having completed the programmed sequence, the application program of the central processing unit 1 automatically repeats the first test again, proceeding to switch on the visible light source 11; the light flux level is automatically adjusted by unit 1, or manually by the operator, so as to constrict the pupil 21 of the adelpho-eye (and, hence, pupil 21 of the eye being examined) adapting itself, for example, to a diameter of approx. 4–5 mm. (mesopic conditions of semi-darkness).

Therefore, the first test is repeated in such conditions and the randomness of the character and/or figure selection avoids test distortion due to memory retention of the patient. Upon termination, the score achieved is memorised together with the new mean pupillary diameter.

The operations described above are afterwards repeated for all the tests of the programmed sequence.

The final stage envisages the repetition of all the tests performed in photopic conditions (pupils 21 constricted to a diameter of approx. 2–3 mm.), increasing the light flux of the illumination source 11 until the desired pupillary diameter is reached.

Upon termination of the tests and measurements, the operator thus has a complete set of results available, obtained from the patient in all the tests performed by him/her, depending on the pupillary diameter actually measured. The whole measurement stage is then repeated in an identical manner on the other eye of the subject being examined.

In alternative embodiments of the invention, the measurement may not require constant operator presence for the entire duration, since the whole procedure may be performed automatically by the central processing unit 1 and patient responses can be picked up by microphone, digitalised and recognised by a voice recognition application program, housed in the same central processing unit 1.

The interaction between the measurement apparatus, according to the invention, and the patient can be, after all, increased through the use of headphones and/or voice synthesis apparatus able to guide the patient during the execution of the whole examination.

The description makes clear the characteristics of the apparatus for measuring visual performance, which is the subject of the present invention, with its advantages being likewise apparent.

In particular, these are represented by:
realisation of multiple visual functionality tests in controlled and variable pupillary opening conditions of the subject being examined, by controlling the ambient brightness and measurement of the pupillary size under dynamic conditions;
control of optic aberrations by controlling the pupillary diameter during the tests;
possibility of quantifying the same visual performance to different values of pupillary opening, corresponding to respective ambient illumination conditions (darkness, semi-darkness, full light);
adoption of random sequences of characters and/or figures produced by an application program for computers, in order to avoid changes in the outcome of the tests due to memory retention of the patient;
possibility of implementing the apparatus, according to the invention in headset form, with a synthesis and voice recognition device, so as to produce a basically autonomous measurement station which reduces the need for intervention by one or more operators;
possibility of memorising and making available for printing and statistical processing of all the tests results of the patient examined;
Lastly, the usefulness of the apparatus, according to the present invention, proves particularly significant in establishing the basic level of visual performance in patients undergoing refractive surgery to compare its post-surgery development. Besides, the tests performed with the measurement apparatus, according to the present invention, may prove extremely useful for those working in extreme light conditions such as vehicle drivers and airline pilots.

It is clear, however, that numerous variations can be made to the apparatus for measuring visual performance, subject of the present invention, without leading away from the innovative principles of the invention, as it is clear that, in the practical implementation of the invention, any materials, forms and dimensions of the details illustrated may be replaced with other technically equivalent ones.

What is claimed is:

1. An apparatus for measuring visual performance for ophthalmologic examinations, comprising:

an electronic processing unit configured to produce at least one of characters and graphic signs;

at least a shutter of optic paths relating to eyes of a subject being examined, said shutter configured to obstruct at least one eye at a time;

a first visualization device of said at least one of characters and graphic signs, controlled by a convertor, connected to said electronic processing unit;

a device of observation and measurement of dimensions of at least one pupil of the subject being examined, configured to produce an image signal sent to an electronic analysis circuit, digitally converted, and to transmit, to said electronic processing unit, information relating to the dimensions of the at least one pupil;

a first illumination device of the at least one pupil, through invisible electromagnetic radiation, controlled to be working at an eye being examined in the subject; and a second illumination device of the at least one pupil, through visible electromagnetic radiation, controlled to prove working next to at least one eye not being examined of the subject, and whose emitted light flux is adjustable by said electronic processing unit.

2. A measuring apparatus as in claim 1, wherein said electronic processing unit produces the at least one of the characters and graphic signs on at least a second visualization display.

3. A measuring apparatus as in claim 1, further comprising a first optic system configured to form an image of said first visualization device, and a second optic system, configured to split up said image of the first visualization device on at least two channels with equal brightness, to allow binocular observation of said image by the subject being examined.

4. A measuring apparatus as in claim 3, wherein said second optic system includes an optic conjugation system, including lenses and mirrors.

5. A measuring apparatus as in claim 4, wherein said optic conjugation system includes compensation means for at least one of spherical and cylindrical refractive errors of an observer, within an appropriate interval of values, afocal systems, configured for compactation of optic paths, optic filters of neutral or chromatic type, and means of fine focusing adjustment of said image.

6. A measuring apparatus as in claim 3, wherein said image is formed on a plane, set to infinity, with a definable angular magnification.

7. A measuring apparatus as in claim 3, wherein said first optic system includes means for varying separation between observation eyepieces of the subject being examined, adapting the means for varying to an interpupillary distance of the subject.

8. A measuring apparatus as in claim 3, wherein the apparatus is firmly fixed on a height adjustable motorized rest platform with chin and head rests.

9. A measuring apparatus as in claim 1, wherein said device of observation and measurement is envisaged next to at least one of the eyes of the subject.

10. A measuring apparatus as in claim 1, wherein said first visualization device includes at least one of a cathode-ray tube, a liquid crystal display, a plasma viewer, and an electroluminescent viewer.

11. A measuring apparatus as in claim 1, wherein said device of observation and measurement includes one of a televisual sensor and matrix detector, matched with a lens to focus the at least one pupil of the subject being examined.

12. A measuring apparatus as in claim 1, wherein said electronic processing unit is further configured to detect information relating to a diameter and area of the at least one pupil of the subject being examined.

13. A measuring apparatus as in claim 1, wherein said device of observation and measurement takes a measurement of the dimensions of the at least one pupil in a sequential manner in time.

14. A measuring apparatus as in claim 1, wherein said device of observation and measurement includes a computer graphics board, configured to digitally store data of an image of the at least one pupil, together with said electronic processing unit, by an image analysis application program.

15. A measuring apparatus as in claim 1, wherein said device of observation and measurement is set at an angle with respect to a direction defined by a visual axis of the eyes of the subject.

16. A measuring apparatus as in claim 1, wherein said device of observation and measurement is collinear with respect to a direction defined by a visual axis of the eyes of the subject and includes at least one dichroic mirror separating a spectral part of electromagnetic radiation coming from the eyes of the subject being examined.

17. A measuring apparatus as in claim 1 wherein said first illumination device of the at least one pupil uses infrared electromagnetic radiation, to provide a sufficient level of illumination for said device of observation and measurement of the dimensions.

18. A measuring apparatus as in claim 5, wherein said first illumination device of the at least one pupil comprises infrared LEDs and means for polarizing emission of radiation.

19. A measuring apparatus as in claim 12, wherein said second visible light illumination device comprises one of visible light incandescence bulbs, LEDs, and fluorescent tubes, so that a maximum light flux emitted is configured to induce a marked constriction of the at least one pupil and not subjected to examination.

20. A measuring apparatus as in claim 12, wherein said second illumination device is set according to an angled direction with respect to a vision axis, to not interfere with central visions of both the eye being examined and the eye not being examined.

21. A measuring apparatus as in claim 1, integrated, at least partially, on a headset used for indirect ophthalmoscope in ophthalmology or for virtual reality, wearable by the subject being examined.

22. A measuring apparatus as in claim 21, wherein said headset is adjustable to all types of head shapes, said headset being securely fixed on the head of the subject being examined.

23. A measuring apparatus as in claim 1, wherein said first visualization device is placed a set distance from the subject being examined, while said device of observation and measurement of dimensions, said first and second illumination devices, and said shutter are integrated in a headset used for indirect ophthalmoscope in ophthalmology or virtual reality, wearable by the subject being examined, said headset and said first visualization device being connected to said electronic processing unit.

* * * * *